United States Patent [19]

Canavesi et al.

[11] 4,331,567

[45] May 25, 1982

[54] PROCESS FOR PREPARING CATALYSTS BASED ON MOLYBDENUM AND IRON OXIDES

[75] Inventors: Roberto Canavesi, Bollate; Ferdinando Ligorati, Usmate; Roberto Ghezzi, Cusano Milanino; Roberto Clemente, Milan, all of Italy

[73] Assignee: Euteco Impianti S.p.A., Milan, Italy

[21] Appl. No.: 218,224

[22] Filed: Dec. 19, 1980

[30] Foreign Application Priority Data

Dec. 19, 1979 [IT] Italy ............................... 28218 A/79
Dec. 19, 1979 [IT] Italy ............................... 28224 A/79

[51] Int. Cl.$^3$ ............................................. B01J 23/88
[52] U.S. Cl. ......................................................... 252/470
[58] Field of Search ................... 252/470; 423/54, 139

[56] References Cited

U.S. PATENT DOCUMENTS 3,459,807  8/1969  Aglietti et al. ................... 252/470 X
3,983,073  9/1976  Trifiro et al. ....................... 252/470

FOREIGN PATENT DOCUMENTS 55-130821  10/1980  Japan ..................................... 423/54
55-130822  10/1980  Japan ..................................... 423/54

*Primary Examiner*—W. J. Shine
*Attorney, Agent, or Firm*—Sughrue, Mion, Zinn, Macpeak and Seas

[57] ABSTRACT

Preparation of a catalyst based on molybdenum and iron oxides by precipitation from a soluble molybdenum compound and a soluble ferric salt, with separation of the precipitate from its mother waters and washing with deionized water.

Molybdic ions are recovered from the mother waters and washing waters by contacting the latter with a salified anionic exchange resin, which is then contacted with aqueous alkali metal hydroxide to yield an aqueous solution of alkali metal molybdate.

The molybdenum thus recovered may be recycled to the precipitation step upon conversion of the molybdate into molybdic acid by treatment with a strong cationic exchange resin, and possible conversion of the acid into ammonium paramolybdate.

16 Claims, No Drawings

PROCESS FOR PREPARING CATALYSTS BASED ON MOLYBDENUM AND IRON OXIDES

The present invention relates to improvements in the process for the preparation of catalysts based on molybdenum and iron oxides, and possibly also cobalt or nickel, oxide, active in the preparation of formaldehyde by oxidation of methanol.

The catalysts for the oxidation of methanol, based on molybdenum and iron oxides, are known in the art and are described for example in U.S. Pat. No. 1,913,405. These catalysts have, as is known, a strong tendency to disaggregate, and to overcome this drawback, it was suggested to form an inactive catalyst precursor, but with mechanical characteristics such as to permit its delivery and charging into the oxidation reactor. Activation of the catalyst is then carried out into the reactor by heating at elevated temperature in the presence of air.

It was also suggested to use a support for the catalyst, and more particularly a support of sinterized iron oxide, or of carbide, generally silicon carbide. For a better understanding, reference is made to the specifications of U.S. Pat. Nos. 2,812,308 and 2,812,309.

It is currently a common practice to prepare the catalysts based on molybdenum and iron oxides by means of a process which comprises essentially the following series of steps:
  precipitation in an aqueous medium from a soluble molybdate and a soluble ferric salt;
  separation and washing of the precipitate, and reduction of the water content of the washed precipitate;
  conversion of the solid thus obtained into bodies of a suitable shape and size;
  drying of said bodies and calcining at elevated temperature.

The processes shown in the following patents are based on such a general scheme:
  Canadian Pat. No. 619,043, in which there is described a particular treatment of the solid in the plastic state in a step preceding the thermal treatment step;
  U.S. Pat. No. 3,459,807, which describes the reduction of the water content of the precipitated and washed solid by a pressing treatment;
  Belgian Pat. No. 601,600, which suggests the addition of small amounts of cobalt oxide to the molybdenum and iron oxides;
  U.S. Pat. No. 3,464,931, which describes a forming treatment of the dried solid into hollow cylinders.

The processes referred to, although yielding satisfactory catalysts, essentially present drawbacks deriving from the loss of molybdenum compounds solubilized in the aqueous precipitation medium and in the washing waters for the precipitate.

In particular, said waters generally contain up to about 1000 mg/l of molydbenum, expressed as metal, generally in the form of soluble molybdate. A complete recovery of said molybdenum is thus important, because of its high cost, and therefore for the economics of the process, or for ecological reasons. Moreover, the ammonium ion content of said waters is typically of the order of 50-5000 ppm and must be reduced to values lower than 0.05 ppm to permit discharge of said waters, again for ecological reasons.

These desirable results are obtained according to the present invention by preparing the catalysts based on molybdenum and iron oxides by means of a process which comprises the following series of steps:
  precipitation in an aqueous medium from a soluble compound of molybdenum and a soluble ferric salt;
  separation of the precipitate from its mother waters and washing of the precipitate with deionized water; and
  processing of the washed precipitate to obtain the final active catalyst; said process being characterized in that:
  the mother waters and/or the washing waters of the precipitate are contacted with a weak anionic exchange resin salified with an acid, thereby to block on said resin molybdic ions present in said waters; and
  said molybdic ions are then recovered in the form of alkali metal molybdate by contacting said resin containing the molybdic ions with an aqueous solution of alkali metal hydroxide, preferably sodium hydroxide.

The solution of alkali metal molybdate thus recovered may be recycled to the precipitation step, upon conversion into the desired molybdenum compound used as starting material at the precipitation step.

In a first embodiment of the process of the present invention, in which a soluble molybdate is used as the starting material at the precipitation step, the aqueous solution of alkali metal molybdate thus obtained is preferably contacted with a strong cationic exchange resin, thereby to block on the resin the sodium ions and to recover an aqueous solution of molybdic acid; and molybdic acid is generally converted into ammonium paramolybdate by addition of the suitable quantity of ammonia to the acid solution, with subsequent recycle of the aqueous solution of ammonium paramolybdate to the precipitation step.

This mode of operating is preferred, insofar as ammonium paramolybdate is the soluble molybdate most suited and commonly used in the preparation of catalysts based on molybdenum and iron oxides.

In this first embodiment iron molybdate, or in an equivalent manner molybdenum and iron oxides are firstly precipitated from dilute solutions of soluble molybdates and soluble ferric salts. Usually, ammonium paramolybdate and ferric chloride are used for the purpose. The precipitate thus obtained is separated from the mother waters by decanting, centrifuging or filtration, and is then washed with deionized water to remove the soluble salts formed in the reaction.

According to a preferred embodiment, an aqueous solution containing from 2 to 5% by weight of ferric chloride is gradually added to an aqueous solution containing from 3 to 7% by weight of ammonium paramolybdate and a sufficient amount of hydrochloric acid to ensure a molar ratio between acid and ammonium paramolybdate of from 12:1 to 18.1. The overall atomic ratio between molybdenum and iron is also maintained to values of from 2.5:1 to 3.2:1. There is obtained in this manner the desired precipitation, and the resulting suspension is heated at a temperature of 45°-55° C. The pH value is then set to a value of about 1 by means of the addition of aqueous hydrochloric acid, and the precipitate is separated. Said precipitate is washed with deionized water until the content of ammonium ion in the washing waters is reduced to values below about 0.2% by weight.

The mother waters combined with the washing waters typically contain a quantity of molybdenum of the order of 600–1000 mg/l, expressed as metallic molybdenum, and they are submitted to the treatment with a salified weak anionic exchange resin in accordance with the present invention.

According to a second embodiment of the present invention, molybdic acid is used as the soluble molybdenum compound at the precipitation step.

In this case, the precipitation from molybdic acid and from a ferric salt, such as ferric chloride, is typically carried out at a pH value of the order of 1–2, and at such pH values the solubility of iron molybdate (or in an equivalent manner of molybdenum and iron oxides) is relevant. Therefore, the mother waters and washing waters contain a quantity of molybdenum higher than in the first embodiment. However, said second embodiment permits the drawbacks deriving from the use of molybdates as starting compounds, and in particular from the presence of ammonium ions in the mother and washing waters, to be avoided.

In said second embodiment, the aqueous solution of alkali metal molybdate obtained by treatment with the weak exchange resin is also preferably contacted with a strong cationic exchange resin, as in the first embodiment, to recover an aqueous solution of molybdic acid. This mode of operating is again preferred, insofar as the above treatment permits a complete recovery of molybdenum in the form of an aqueous solution of molybdic acid directly recyclable to the precipitation step.

In this second embodiment, iron molybdate or in an equivalent manner molybdenum and iron oxides are precipitated from dilute solutions of molybdic acid and of soluble ferric salts. Usually, ferric chloride is used for the purpose. The precipitate thus obtained is separated from its mother waters by decanting, centrifuging or filtration, and is then washed with deionized water. According to a preferred embodiment, an aqueous solution containing from 2 to 5% by weight of ferric chloride is gradually added to an aqueous solution containing from 3 to 7% of molybdic acid, and the overall atomic ratio between molybdenum and iron is maintained at a value of from 2.5:1 to 3.2:1.

There is obtained in this manner the desired precipitation, and the precipitate is washed with deionized water until the chlorine ion content of the water is reduced to values lower than 100 ppm.

The precipitation waters, combined with the washing waters, typically have a molybdenum content of the order of 1000–1200 mg/l, expressed as metallic molybdenum, and are submitted to the treatment with a weak anionic exchange resin in accordance with the present invention.

The weak anionic exchange resins are those, known in the art, which contain weak basic groups such as $-NH_2$, $-NHR$, $-NR_2$, where R is an alkyl with from 1 to 3 carbon atoms. These anionic resins may be obtained by condensation of aniline or m-phenylenediamine with formaldehyde. It is, however, preferred to use anionic exchange resins based on a matrix of polystyrene cross-linked with divinylbenzene, which are generally obtained by treating a cross-linked and chloromethylated polystyrene with ammonia, or with a primary or secondary amine. Generally, these anionic resins have an exchange capability of from 2 to 2.5, expressed in equivalents/liter.

Examples of suitable commercial anionic resins are DUOLITE A-7 (of the Chemical Process Company), DUOLITE ES 365 (of the Chemical Process Company), LEWATIT MP 62 (of the Bayer Company), AMBERLITE IRA 93 (of the Rohm & Haas Company) and similar.

Said anionic resins are used in the form salified with an acid such as hydrochloric acid, hydrobromic acid, sulphuric acid and nitric acid, and therefore the anionic resins indicated above are conditioned and activated, before use, by means of a process which is preferably of the following type:
- conditioning in deionized water for 10–15 hours and washing with deionized water to prepare the bed of resin,
- treatment with an aqueous alkali metal hydroxide (such as sodium hydroxide),
- washing with deionized water,
- salifying by contact with an aqueous acid chosen from those indicated above (acid concentration in the solution: 3–7% by weight),
- washing with deionized water.

According to the process of the present invention, the waters containing in solution iron mobyldate, are contacted with the salified weak anionic resin to block the molybdate ions on the latter by means of a double exchange reaction. Preferably, the anionic resin is arranged in the form of a fixed bed, and the solution is percolated at a rate of from 5 to 15 volumes per volume of resin and per hour. This treatment is preferably carried out at ambient temperatures (20°–25° C.), even if it is generally possible to use temperatures within a broader range, such as from 10° to 40° C.

By operating under these conditions molybdenum (or better the molybdic ion) is retained on the anionic resin with a yield of at least 95%, and an eluate is discharged which is essentially formed of aqueous ferric salt, free from molybdenum or containing only traces of molybdenum. Typically, such an eluate contains molybdenum (expressed as metal) in amounts not exceeding 100 ppb.

It should be noted that the anionic resin retains a quantity of molybdic ion equivalents higher than the capability attributable to said resin, and generally a quantity equal to about 1.5 times said capability. This surprising fact permits the recovery of molybdenum to be carried out in an economical manner, with relatively small amounts of resin.

Conveniently, the elution of the molybdic ions from the resin is carried out by means of an aqueous alkali metal hydroxide, preferably aqueous sodium hydroxide. Preferably an aqueous solution of alkali metal hydroxide with a concentration of from 3 to 20% by weight is percolated through the bed of anionic resin (previously washed with deionized water), at a rate from 1 to 10 volumes per volume of resin and per hour, operating at ambient temperature (20°–25° C.) or more generally within a range of temperature of from 10° to 40° C. At the end of the percolation, the anionic resin is washed with deionized water and an aqueous solution of alkali metal molybdate is recovered.

The anionic resin which is obtained after this treatment must be regenerated to its salified form, and to this end the resin is treated with an aqueous solution of an acid such as hydrochloric acid, sulphuric acid, nitric acid, etc., having typically a concentration of 3–7% by weight, and this is followed by a washing with deionized water in a quantity typically of the order of 2 volumes for each volume of resin bed.

As already indicated, the alkali metal molybdate is preferably converted into molybdic acid or ammonium paramolybdate, which is then recycled to the precipitation step. To this end, according to a preferred embodiment of the present invention, the aqueous solution of alkali metal molybdate is contacted with a strong cationic exchange resin in the acid form, also called hydrogen form, thus to obtain an aqueous solution of molybdic acid. Suitable strong cationic exchange resins are those which carry sulphonic or methylene sulphonic groups. The most important among these are the cationic exchange resins obtained by sulphonation of polystyrene cross-linked with divinylbenzene. These cationic exchange resins generally have an exchange capability of from 1 to 3 equivalents per liter of resin.

Examples of commercial strong cationic resins are DUOLITE C 264 (of the Chemical Process Company), DUOLITE C 265 (of the Chemical Process Company), AMBERLITE IR 124 (of the Rohm & Haas Company) and similar.

These cationic resins may be conditioned and converted into their hydrogen form before use by means of a treatment of the following type:

conditioning in deionized water for 10-15 hours and subsequent washing with deionized water to prepare the bed of resin, treatment with an aqueous solution of a strong acid (such as HCl, $H_2SO_4$, $HNO_3$) with a concentration of 2-40% by weight, at a percolation rate of 0.5-8 volumes per volume of resin and per hour, washing with deionized water until the pH is neutral, and at a rate of 10-20 volumes of water per volume of resin and per hour.

According to a preferred embodiment of the present invention, the aqueous solution of alkali metal molybdate is percolated through the cationic resin thus treated, arranged in the form of a fixed bed, at a rate of from 0.5 to 3 volumes per volume of resin and per hour, operating at ambient temperature (20°-25° C.) or more generally within a range of temperatures of from 10° to 80° C. At the end of the percolation, the cationic resin is washed with deionized water, and there is recovered an aqueous solution of molybdic acid, which may be recycled to the precipitation step.

According to the aforesaid first embodiment, the acid is then neutralized by means of ammonia (generally by addition of aqueous ammonia) and the solution of ammonium paramolybdate thus obtained is recycled to the precipitation step.

The cationic resin may be regenerated to its hydrogen form by treatment with aqueous acid and washing with deionized water in the manner already indicated.

According to a further embodiment of the present invention, the treatment of the mother waters and/or washing waters is combined with a treatment for the recovery of molybdenum from the exhausted catalyst. In particular, the exhausted catalyst based on molybdenum and iron oxides, and possibly also on cobalt or nickel oxide, may be submitted to a treatment comprising the following series of steps:

the exhausted catalyst is reduced to a powder with an average particle size preferably of the order of 300 microns;

said powder is optionally heated at a temperature of 150° to 200° C. for a period of the order of 0.5-20 hours in the presence of air;

the powder is contacted with an aqueous solution of alkali metal hydroxide (preferably aqueous sodium hydroxide), operating preferably at a temperature of from 20° to 70° C. and for a period of from 0.5 to 4 hours, thereby to obtain an aqueous solution of alkali metal molybdate and a residual solid comprising iron hydroxide and possibly also cobalt or nickel hydroxide; this treatment may be carried out by using at least part of the aqueous solution of alkali metal molybdate obtained in the treatment of the mother waters and/or washing waters in the preparation of the catalyst, upon suitable addition of alkali metal hydroxide;

the residual solid is filtered off and possibly washed with deionized water, and there is recovered an aqueous solution of alkali metal molybdate, which may be treated with a cationic exchange resin in the manner already described, to obtain molybdic acid.

This treatment may be combined with that of the alkali metal molybdate solution obtained in the preparation of the catalyst, and the molybdic acid thus obtained is recycled to the precipitation step, or is neutralized by means of the necessary quantity of ammonia, with subsequent recycle of the ammonium paramolybdate solution to the precipitation step.

The remaining part of the process for the preparation of the catalyst is carried out according to know methods. By way of example, the preparation of the catalyst in the form of uneven granules may be carried out according to the following scheme:

the water content of the washed precipitate is reduced to a value of from 30 to 40% by weight by filtrattion and pressing, thus to obtain a cake;

said cake is ground to form granules;

said granules are dried by heating gradually to a temperature below 100° C.;

the dried granules are calcined by gradual heating to a temperature not exceeding 400° C. (for example from 300° to 400° C.).

According to a further embodiment a catalyst containing cobalt oxide in addition to molybdenum and iron oxides is prepared in the form of bored bodies. More particularly, the preparation may be carried out as follows:

an aqueous suspension is prepared by mixing an aqueous solution containing from 12 to 18% by weight of cobalt chloride or cobalt nitrate, heated at a temperature of from 60° to 70° C., with an aqueous solution containing from 5 to 10% by weight of molybdic acid or ammonium molybdate;

the precipitate thus obtained is mixed in suitable proportions with the precipitate of molybdenum and iron oxides obtained as described hereinbefore;

the water content of the homogenized precipitates is reduced down to a quantity of from 30 to 40% by weight, to obtain a conglomerate;

said conglomerate is ground to particles with a size of about 0.3-0.85 mm;

said particles are dried at a temperature not exceeding 100° C., thus to further reduce the water content to values of from 5 to 10%;

said dried particles are formed into hollow cylinders; and said hollow cylinders are calcined.

These two embodiments have been shown by way of illustrative and non-limitative examples, since the processing of the precipitate does not constitute the fundamental aspect of the present invention.

It is also possible to introduce an inert material in the catalyst, for example titanium dioxide, or fullers earth such as that commercially known under the name Florex. This inert material is preferably introduced in the form of a fine powder (granules with a size of the order of 1–30 microns) which is homogenized with the precipitates of the oxides of molybdenum, iron and possibly also cobalt or nickel. The quantity of support is not critical and may reach a percentage of the order of about 50% by weight on the final catalyst.

The catalysts of the present invention are used in the form of a fixed bed in the oxidation process of methanol to formaldehyde. Generally, in said process there is fed to the catalyst a gaseous stream containing from 3 to 15% in volume of methanol and from 5 to 20% in volume of oxygen, the remaining percentage consisting of inert gases, operating at a temperature of from 200° to 400° C. and with a space velocity of from 4000 to 15000 normal volumes of gas per volume of catalyst and per hour.

Under these conditions, the conversion referred to methanol is generally higher than 97% with a selectivity for formaldehyde at least equal to 95% with respect to the converted methanol.

The following experimental Examples are illustrative and non-limitative for the invention.

EXAMPLE 1

There is recovered molybdenum from an exhausted catalyst used in the oxidation of methanol to formaldehyde, having the following composition by weight: 81.5% of $MoO_3$, 16.7% of $Fe_2O_3$, and 1.8% of $CoO$.

The catalyst is ground to reduce it into a powder with a size of the order of 300 microns, and the powder is heated at 200° C. for 2 hours in air. 300.2 g of the powder are treated with 1132 g of aqueous solution containing 12% by weight of sodium hydroxide. The whole is maintained under agitation for 2 hours at ambient temperature (20°–25° C.). The solid residue is then filtered off and washed. There are thus recovered 1.4 l of aqueous solution containing 163 g of molybdenum expressed as metal. The solid residue amounts to 55.5 g and is essentially formed of iron and cobalt hydroxides. The solution is percolated through 4 liters of cationic exchange resin DUOLITE C 265 of the Chemical Process Company, said resin carrying sulphonic groups and being previously pre-conditioned as described hereinbefore. The rate of percolation is equal to one volume of solution per volume of resin and per hour, and the operation is carried out at ambient temperature (20°–25° C.). At the end of the percolation, the column is washed with deionized water, and the percolated solution and the washing waters are combined. There are thus obtained 4 l of aqueous solution of molybdic acid, having a molybdenum content of 41 g/l. The recovery yield of molybdenum is practically quantitative.

The molybdic acid thus obtained is converted into ammonium paramolybdate by means of the addition of 51 g of ammonium hydroxide, and the volume of the solution is brought to 5 l by addition of water.

The solution thus obtained is heated at 50° C. and 3.3 l of aqueous solution containing 165 g of ferric chloride hexahydrate are added under agitation. Upon cooling of the suspension, the latter is washed by decantation with 24 l of water and the whole is filtered. There are obtained 852 g of precipitate containing 70% of water, and 32 l of a solution containing 20.5 g of molybdenum, expressed as metal. The solution is treated as described in the following Example 2. The precipitate is converted into a catalyst under conditions similar to those described in Example 1 of U.S. Pat. No. 3,464,931. In the oxidation of methanol carried out according to the procedure described in Example 2 of said U.S. patent, there was obtained a molar conversion of methanol equal to 98%, with a molar selectivity for formaldehyde of 96% with respect to the converted methanol.

EXAMPLE 2

32 l of the aqueous solution obtained as described in Example 1, are percolated through 500 ml of weak anionic exchange resin DUOLITE A-7 of the Chemical Process Company, said resin carrying amino groups, prevalently secondary, and being salified with hydrochloric acid according to the conditions described hereinbefore. The percolation rate is equal to 10 volumes of solution per volume of resin and per hour, and the operation is carried out at ambient temperature (20°–25° C.). The molybdic ions are thus fixed on the resin by means of a double exchange. The eluate discharged is formed of aqueous ferric chloride with traces only of molybdenum (quantity not exceeding 100 ppb). The molybdic ions fixed on the resin are then recovered in the form of aqueous sodium molybdate by percolating through the resin 0.7 liters of a 4 N aqueous solution of sodium hydroxide at a rate of 4 volumes of solution per volume of resin and per hour, operating at ambient temperature (20°–25° C.). At the end of the percolation, the resin is washed with a little deionized water, and there is recovered 1 liter of alkaline solution containing 19.5 g of molybdenum, expressed as metal. The solution thus obtained is admixed with 264.3 g of exhausted catalyst, ground and heat-treated as described in Example 1, and with 0.5 l of aqueous solution containing 55.9 g of sodium hydroxide. The whole is maintained under agitation for 2 hours at ambient temperature (20°–25° C.). The residual solid is filtered off and washed, thus recovering 2 l of a solution containing 163 g of molybdenum. The solution thus obtained is percolated through a column containing 4 l of the cationic resin in the acid form described in Example 1, at a rate of 1 volume per volume of resin and hour. At the end of the percolation, the column is washed with deionized water, and the percolated solution and the washing waters are combined.

There are thus obtained 4 l of aqueous solution of molybdic acid having a molybdenum content of 163 g. The recovery yield of molybdenum is practically quantitative. The solution of molybdic acid has a sodium content of the order of 10 ppm.

The molybdic acid thus obtained is converted into ammonium paramolybdate by adding 51 g of ammonium hydroxide, and the total volume of the solution is brought to 5 l by addition of deionized water.

The solution thus obtained is heated at 50° C., and 3.3 l of aqueous solution containing 165 g of iron chloride hexahydrate are added under agitation. After cooling, the precipitate thus obtained is washed by decantation with 24 l of deionized water and is then filtered off. There are thus obtained 852 g of precipitate with a water content of about 70% by weight, and 32 l of aqueous solution containing 20.5 g of molybdenum.

The precipitate is used to prepare a catalyst as shown in Example 1, and said catalyst has activity and selectivity values similar to those of the catalyst obtained in said Example 1.

Molybdenum is recovered from the aqueous solution by operating as already indicated.

EXAMPLE 3

One liter of strong cationic exchange resin DUOLITE C 264 of the Chemical Process Company is kept for 12 hours in a bath of deionized water. The resin is then charged into a glass column with an internal diameter of 40 mm and a height of 1.5 m. The resin is washed in counter-current with deionized water to settle the bed and remove possible impurities present therein. The resin is then fed with 2 l of aqueous solution containing 109.5 g of hydrochloric acid at a rate of 1 volume of solution per volume of resin and per hour. Washing is then carried out with deionized water until the pH of the eluate is neutral.

0.4 l of aqueous solution of sodium molybdate obtained by alkaline attack of an exhausted catalyst as described in Example 1, are percolated through the resin. The solution, which contains 48 g of molybdenum as sodium molybdate dihydrate, is percolated at a rate of one volume per volume of resin and per hour. At the end of the percolation the resin is washed with 1470 ml of deionized water. There are discarded the first 500 ml of liquid issuing from the resin, which typically are free from molybdenum and sodium. The percolated solution and the washing waters are recovered and combined, thus obtaining 1370 ml of aqueous solution of molybdic acid with a molybdenum content of 35 g/l. The recovery yield of molybdenum is thus practically quantitative. The solution also contains traces of sodium (about 10 ppm). Molybdic acid is converted into ammonium paramolybdate and the salt is used in the preparation of the catalyst as already indicated.

EXAMPLE 4

250 ml of weak anionic exchange resin DUOLITE A-7 are kept for 12 hours in deionized water. The resin is then charged into a glass column with an inner diameter of 20 mm. and a height of 1.5 m. The resin is washed in counter-current with deionized water to settle the bed and to remove possible impurities present therein. There is then percolated through the resin 1 liter of aqueous solution containing 40 g of sodium hydroxide, at a rate of 4 volumes per volume of resin and per hour, and washing with 0.5 l of deionized water is then carried out.

The resin is then salified by feeding in counter-current an aqueous solution containing 36.5 hydrochloric acid, at a rate of 4 volumes of solution per volume of resin and per hour, and washing with 0.5 l of deionized water is then carried out.

There are percolated through the salified resin 18 l of aqueous solution containing 0.56 g/l of dissolved molybdenum in the form of iron molybdate, obtained as mother waters and washing waters in the precipitation step of the preparation process of the catalyst. The percolation is carried out at a rate of 10 volumes of solution per volume of resin and per hour, operating at ambient temperature (20°–25°).

Under these conditions the molybdic ions are fixed on the resin by double exchange reaction, and an eluate is discharged essentially formed of aqueous ferric chloride, practically free from molybdenum (molybdenum content of the order of 100 ppb).

The resin is then treated with 1 liter of aqueous solution containing 40 g of sodium hydroxide, at a percolation rate of 4 volumes of solution per volume of resin and per hour, and washing with 250 ml of deionized water is then carried out. There is recovered 1 liter of aqueous solution of alkali metal molybdate having a molybdenum content of 9.6 g and with an overall recovery yield of 95%.

The sodium molybdate is converted into molybdic acid and the latter into ammonium paramolybdate in the manner already indicated.

The resin is submitted to a salifying treatment by percolating 0.6 l of aqueous solution containing 22 g of hydrochloric acid, at a rate of 4 volumes per volume of resin and per hour. After washing with 0.5 l of deionized water the salified resin is ready for a new cycle.

EXAMPLE 5

In the preparation of a commercial charge of catalyst based on molybdenum, iron and cobalt oxides according to the embodiment described hereinbefore, there are obtained at the precipitation step 453 l of mother waters and washing waters having a molybdenum content of 560 mg/l. These waters are percolated through a column having an inner diameter of 60 mm, containing 3 liters of weak anionic resin DUOLITE A-7 of the Chemical Process Company, said resin being salified with hydrochloric acid. The percolation is carried out at ambient temperature (20°–25° C.) and at a rate of 10 liters of solution per liter of resin and per hour. Under these conditions, the liquid issuing from the column contains on an average 5 mg/l of molybdenum, expressed as metal. There are then passed through the resin 1.7 l of 3 N aqueous solution of sodium hydroxide, at a rate of 4 volumes per volume of resin and per hour, still operating at ambient temperature (20°–25° C.).

A washing with water is carried out and there is recovered an aqueous solution of sodium molybdate with a molybdenum content of the order of 90 g/l.

This solution is percolated through a pre-conditioned cationic exchange resin DUOLITE C 265 of the Chemical Process Company, under the conditions described in Example 1. Washing with deionized water is carried out and there is recovered an aqueous solution of molybdic acid with a molybdenum content of the order of 30 g/l. The acid is salified with aqueous ammonia to yield an aqueous solution of ammonium paramolybdate.

EXAMPLE 6

There is recovered molybdenum from an exhausted catalyst used in the oxidation of methanol to formaldehyde, having the following composition by weight: 81.5% of $MoO_3$, 16.7% of $F_2O_3$, and 1.8% of CoO. The catalyst is ground to reduce it into a powder with a size of the order of 300 microns, and the powder is heated at 200° C. for 2 hours in air. 328 g of the dried powder are contacted with 1287.6 g of aqueous solution containing 12% by weight of sodium hydroxide. The whole is maintained under agitation for 2 hours at ambient temperature (20°–25° C.). The solid is then filtered off and washed with deionized water, and there is recovered a total amount of 1,500 ml of aqueous solution containing 178.1 g of molybdenum, expressed as metal. The solution thus obtained is percolated through a column containing 4 liters of strong cationic exchange resin in the acid form DUOLITE C 265 of the Chemical Process Company. The resin which carries sulphonic groups, is conditioned before use under the conditions shown hereinbefore. The solution of sodium molybdate is percolated through the resin at a rate of one volume of solution per volume of resin and per hour, operating at ambient temperature (20°–25° C.). At the end of the percolation, the column is washed with deionized water, and the percolated liquid is combined with the washing liquid, thus obtaining 5 l of aqueous solution of molybdic acid with a molybednum content of 35.6 g/l.

The recovery yield of molybdenum is practically quantitative.

The solution thus obtained is heated at 50° C., and there are added under agitation 3.3 l of aqueous solution containing 180.3 g of ferric chloride hexahydrate. There is formed a precipitate which, upon cooling of the suspension, is washed by decanting with 24 l of water, and then filtered.

There are thus recovered 852 g of precipitate containing 70% by weight of water, and 32 liters of aqueous solution containing 35.6 g of molybdenum, expressed as metal.

The aqueous solution is treated as described in the following Example 7. The precipitate is converted into a catalyst based on molybdenum, iron and cobalt oxides, under conditions similar to those described in Example 1 of U.S. Pat. No. 3,464,931. This catalyst, used in the oxidation of methanol to formaldehyde under the conditions shown in Example 2 of said U.S. patent, has afforded a methanol conversion of 98.1% molar, with a molar selectivity for formaldehyde of 96.9% with respect to the converted methanol.

EXAMPLE 7

32 liters of the aqueous solution obtained according to Example 6, containing 35.6 g of molybdenum expressed as metal, are percolated through a column containing 900 ml of weak anionic exchange resin known under the commercial name DUOLITE A-7 of the Chemical Process Co.Company. This resin, which contains prevalently secondary amino groups, is previously converted into the corresponding chloride by treatment with aqueous hydrochloric acid according to the embodiment shown hereinbefore. The percolation rate is 10 volumes of solution per volume of resin and per hour, and the operation is carried out at ambient temperature (20°–25° C.). Thus, the molybdic ions are fixed on said resin by means of a double exchange. Upon washing of the resin, the molybdic ions are recovered in the form of sodium molybdate by percolating through the resin one liter of 4 N aqueous solution of sodium hydroxide, at a rate of 4 volumes per volume of resin and per hour. At the end of the percolation, the resin is washed with a little of deionized water, and there are recovered 1.3 l of a solution containing 33.8 g of molybdenum, expressed as metal.

The solution thus obtained is admixed with 265.7 g of exhausted catalyst, ground and dried, and having the composition shown in Example 1, and with 200 ml of aqueous solution containing 20.5 g of sodium hydroxide. The whole is maintained under agitation for 2 hours at ambient temperature (20°–25° C.). The solid residue is filtered off and washed, and there are recovered 2 l of aqueous solution containing 178.1 g of molybdenum. This solution is percolated through a column containing 4 l of the aforesaid strong cationic exchange resin DUOLITE C 265, at a rate of 1 volume per volume of resin and per hour, operating at ambient temperature (20°–25° C.). At the end of the percolation, the column is washed with deionized water, and there is obtained a total amount of 5 l of aqueous solution of molybdic acid containing 178.1 g of molybdenum. The recovery yield of molybdenum is practically quantitative.

The solution thus obtained is heated at 50° C. and there are added under agitation 3.3 l of aqueous solution containing 180.3 g of ferric chloride hexahydrate. After cooling, a washing by decanting with 24 l of water is carried out, with subsequent filtration. There are thus obtained 32 l of a solution containing 35.6 g of molybdenum, and 852 g of precipitate with a water content of the order of 70% by weight.

The solution is submitted to the treatment for the recovery of molybdenum in the form of molybdic acid.

The precipitate is converted into a catalyst as described in Example 1 of U.S. Pat. No. 3,464,931, and used in the oxidation of methanol under the conditions shown in Example 2 of said U.S. patent. The conversion and selectivity values are similar to those achieved in Example 6.

We claim:

1. In a process for preparing a catalyst based on molybdenum and iron oxides and active in the oxidation of methanol to formaldehyde, comprising precipitating said oxides in an aqueous medium from a soluble molybdenum compound and a soluble ferric salt, separating the precipitate from its mother waters and washing said precipitate with deionized water, and processing the washed precipitate to obtain the final active catalyst, the improvement which comprises:

contacting the said mother waters and/or the washing waters of the precipitate with a weak anionic exchange resin salified with an acid, thus to fix on said resin molybdic ions present in said waters; and recovering said molybdic ions fixed on the resin in the form of an aqueous solution of alkali metal molybdate by contacting said anionic resin with an aqueous solution of alkali metal hydroxide.

2. The process of claim 1, wherein said alkali metal hydroxide is sodium hydroxide.

3. The process of claim 1, wherein said weak anionic resin is salified with a strong acid selected from the group consisting of hydrochloric acid, hydrobromic acid, sulphuric acid and nitric acid.

4. The process of claim 1, wherein said weak anionic resin contains weak basic groupings selected from $-NH_2$, $-NHR$ and $-NR_2$ wherein R is an alkyl with from 1 to 3 carbon atoms.

5. The process of claim 1, wherein said weak anionic resin is based on a matrix of polystyrene cross-linked with divinylbenzene.

6. The process of claim 1, wherein said weak anionic resin has an exchange capability of from 2 to 2.5 equivalents per liter.

7. The process of claim 1, wherein said aqueous solution of alkali metal molybdate is recycled to the precipitation step upon conversion of said alkali metal molybdate into the soluble molybdenum compound used at said precipitation step.

8. The process of claim 1, wherein said aqueous solution of alkali metal molybdate is contacted with a strong cationic exchange resin in the acid form, thus to fix on the latter alkali metal ions and to recover an aqueous solution of molybdic acid.

9. The process of claim 8, wherein said cationic resin has an exchange capability of from 1 to 3 equivalents per liter.

10. The process of claim 8, wherein said cationic resin is based on a matrix of polystyrene cross-linked with divinylbenzene and carrying sulphonic or methylene sulphonic groups.

11. The process of claim 8, wherein the aqueous solution of alkali metal molybdate is percolated through the cationic resin at a rate of from 0.5 to 3 volumes per volume of resin and per hour, operating at a temperature of from 10° to 80° C.

12. The process of claim 1, wherein said waters are percolated through the salified anionic resin at a rate of from 5 to 15 volumes of resin and per hour, operating at a temperature of from 10° to 40° C., the molybdic ions being then eluted from the anionic resin by percolating through the latter the aqueous solution of alkali metal hydroxide at a rate of from 1 to 10 volumes per volume of resin and per hour and at a temperature of from 10° to 40° C.

13. The process of claim 8, wherein said soluble molybdenum compound used at the precipitation step is molybdic acid, and said aqueous solution of molybdic acid thus recovered is recycled to the precipitation step.

14. The process of claim 8, wherein said soluble molybdenum compound is ammonium paramolybdate, and said aqueous solution of molybdic acid thus recovered is recycled to the precipitation step upon conversion of the molybdic acid present therein into ammonium paramolybdate by neutralization with ammonia.

15. The process of claim 8, wherein said aqueous solution of alakli metal molybdate is previously combined with a further amount of aqueous alkali metal molybdate obtained from an exhausted catalyst based on molybdenum and iron oxides, and possibly also cobalt or nickel oxide, by a treatment comprising the steps of reducing the exhausted catalyst into a powder, contacting said powder with an aqueous solution of alkali metal hydroxide, thus to obtain an aqueous solution of alakali metal molybdate and a residual solid comprising iron hydroxide and possibly also cobalt or nickel hydroxide, filtering off said residual solid and recovering the aqueous solution of alkali metal molybdate.

16. The process of claim 15, wherein said powder of exhausted catalyst is contacted with an aqueous solution obtained by admixing a suitable quantity of alkali metal hydroxide with at least part of the aqueous solution of alkali metal molybdate obtained by treatment of said mother waters and/or washing waters.

* * * * *